United States Patent
Nishida et al.

(10) Patent No.: US 6,689,923 B2
(45) Date of Patent: Feb. 10, 2004

(54) PERFLUOROOLEFIN-HYDROCARBON HYBRID COMPOUND, METHOD OF PRODUCING THE SAME AND METHOD OF PRODUCING PERFLUOROALKYL RADICAL

(75) Inventors: Masakazu Nishida, Nagoya (JP); Taizo Ono, Nagoya (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/373,113

(22) Filed: Feb. 26, 2003

(65) Prior Publication Data

US 2003/0171628 A1 Sep. 11, 2003

(30) Foreign Application Priority Data

Mar. 7, 2002 (JP) ........................................ 2002-062667

(51) Int. Cl.⁷ ................................................ C07C 21/18
(52) U.S. Cl. ........................ 570/136; 570/124; 570/134; 570/155
(58) Field of Search ................................ 570/136, 124, 570/134, 155

(56) References Cited

U.S. PATENT DOCUMENTS 5,576,431 A    11/1996    Nishida et al.
5,789,606 A    8/1998    Ono et al.

OTHER PUBLICATIONS

"Reactions of highly branched fluoroolefins with methyllithium and methylmagnesium bromide: formations of unexpected polyfluorocyclobutene and polyfluoropentadiene compounds" Nishida, et al., Molecular Structure Design Group, Institute for Structural and Engineering Materials, National Institutes of Advanced Industrial Science and Technology (AIST), 2266–98 Simoshidami, Moriyama–ku, Nagoya 463–8560, Japan, Received Oct. 7, 2002; received in revised form Nov. 7, 2002; accepted Nov. 16, 2002, Journal of Fluorine Chemistry 5867 (2002) 1–4.

U.S. patent application Ser. No. 10/291,699, Taizo Ono et al., filed Nov. 12, 2002.

Primary Examiner—Johann Richter
Assistant Examiner—Elvis O. Price
(74) Attorney, Agent, or Firm—Sughrue Mion, PLLC

(57) ABSTRACT

The present invention provides a perfluoroolefin-hydrocarbon hybrid compound represented by the following general formula (1):

$$[(CF_3)_2CX][(CF_3)_2CY]C=C(CF_3)Z \quad (1)$$

wherein X, Y and Z may be the same or different, and independently represent F or R, excepting that all of X, Y and Z are F, wherein R represents straight chain or branched alkyl and aryl groups having from 1 to 15 carbon atoms. The present invention also provides a method of producing the above compound, and a method of producing a perfluoroalkyl radical by using the above compound as a starting material.

2 Claims, No Drawings

PERFLUOROOLEFIN-HYDROCARBON HYBRID COMPOUND, METHOD OF PRODUCING THE SAME AND METHOD OF PRODUCING PERFLUOROALKYL RADICAL

FIELD OF THE INVENTION

The present invention relates to a perfluoroolefin-hydrocarbon hybrid compound produced by reacting a hexafluoropropene trimer or highly branched perfluoroolefin with an organometallic compound, a method of producing the perfluoroolefin-hydrocarbon hybrid compound, and a method of producing a perfluoroalkyl radical by using the perfluoroolefin-hydrocarbon hybrid compound as a starting material.

BACKGROUND OF THE INVENTION

Highly branched perfluoroalkyl radicals are a kind of carbon radical. While carbon radicals are generally unstable and difficult to isolate due to their carbon atom having one unpaired electron, highly branched perfluoroalkyl radicals have excellent chemical stability or inertness to active chemical species such as acid, alkali and water, and can be isolated through dispersion gas chromatography or the like. Such characteristics make them usable in various industrial applications such as a synthetic intermediate for medicines or agricultural chemicals, a surface-active agent.

The highly branched perfluoroalkyl radicals can also be used as a polymerization initiator in polymer synthesis, a finishing agent, or a reagent for checking the leakage of containers having complicated shapes by taking advantage of their characteristic of releasing a low molecular weight perfluoroalkyl radical such as trifluoromethyl at a temperature of about 90° C. or more. The inventors developed a method of facilitating the release of a low molecular weight radical from a highly branched perfluoroalkyl radical, which is the subject of Japanese Patent Application No. 2001-352475.

As an example of a highly stable perfluoroalkyl radical, perfluoro-(2,4-dimethyl-3-isopropyl-3-pentyl) is disclosed in Japanese Patent Laid-open Publication No. 1-29175. The inventors also developed a method for producing a highly stable radical by fluorinating a highly branched perfluoroolefin, which is the subject of Japanese Patent Application No. 2001-352475. While this method is directed to producing a highly stable perfluoroalkyl radical by fluorinating a corresponding perfluoroolefin, the production process requires the use of a costly material, trialkylperfluoroalkylsilane, and a radical having a complicated structure cannot be synthesized through this method.

SUMMARY OF THE INVENTION

In view of the above problems, it is therefore an object of the present invention to provide an improved method of synthesizing a highly branched perfluoroolefin-hydrocarbon hybrid compound as a precursor of a new highly stable perfluoroalkyl radical from a hexafluoropropene trimer and an organometallic compound of alkali metal or alkali earth metal, and a new method of producing the highly stable perfluoroalkyl radical.

The present invention uses a hexafluoropropene trimer and an organometallic compound of alkali metal or alkali earth metal as starting materials, which are commercially available at a low cost. The kind of alkyl and aryl groups in the above organometallic compound can be selectively changed to produce various kinds of highly branched perfluoroolefin-hydrocarbon hybrid compounds, and the obtained compounds can be fluorinated to produce various kinds of highly stable perfluoroalkyl radicals.

More specifically, the present invention provides a perfluoroolefin-hydrocarbon hybrid compound represented by the following general formula (1):

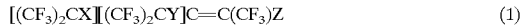
$$[(CF_3)_2CX][(CF_3)_2CY]C=C(CF_3)Z \qquad (1)$$

wherein X, Y and Z may be the same or different, and independently represent F or R, except that all of X, Y and Z are F, wherein R represents straight chain or branched alkyl having from 1 to 15 carbon atoms and aryl groups having from 1 to 15 carbon atoms.

The present invention further provides a perfluoroolefin-hydrocarbon hybrid compound represented by the following general formula (2):

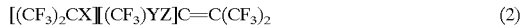
$$[(CF_3)_2CX][(CF_3)YZ]C=C(CF_3)_2 \qquad (2)$$

wherein X, Y and Z may be the same or different, and independently represent F or R, except that all of X, Y and Z are F, wherein R represents straight chain or branched alkyl having from 1 to 15 carbon atoms and aryl groups having from 1 to 15 carbon atoms.

The present invention further provides a method for producing the above perfluoroolefin-hydrocarbon hybrid compound, wherein a hexafluoropropene trimer is reacted with an organometallic compound of alkali metal or alkali earth metal. The organometallic compound is represented by the following general formula (3):

$$RG \qquad (3)$$

wherein R represents a straight chain or branched alkyl and aryl group having from 1 to 15 carbon atoms; and G represents at least one of Li, Na, K, MgX, ZnX and CdX, wherein X represents Cl, Br and I.

The present invention further provides a method for producing a perfluoroalkyl radical, wherein the above perfluoroolefin-hydrocarbon hybrid compounds are fluorinated to form a highly stable perfluoroalkyl radical represented by the following general formula (1R):

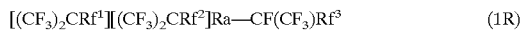
$$[(CF_3)_2CRf^1][(CF_3)_2CRf^2]Ra—CF(CF_3)Rf^3 \qquad (1R)$$

wherein Ra represents a carbon atom having one unpaired electron; and $Rf^1$, $Rf^2$ and $Rf^3$ may be the same or different, and independently represent F or Rf, except that all of $Rf^1$, $Rf^2$ and $Rf^3$ are F, wherein Rf represents a perfluoroalkyl group having from 1 to 15 carbon atoms or perfluorocycloalkyl group having from 1 to 15 carbon atoms.

The present invention further provides a method for producing a perfluoroalkyl radical, wherein the above perfluoroolefin-hydrocarbon hybrid compound is fluorinated to form a highly stable perfluoroalkyl radical represented by the following general formula (2R):

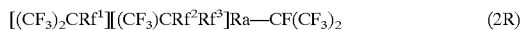
$$[(CF_3)_2CRf^1][(CF_3)CRf^2Rf^3]Ra—CF(CF_3)_2 \qquad (2R)$$

wherein Ra represents a carbon atom having one unpaired electron; and $Rf^1$, $Rf^2$ and $Rf^3$ may be the same or different, and independently represent F or Rf, except that all of $Rf^1$, $Rf^2$ and $Rf^3$ are F, wherein Rf represents a perfluoroalkyl group having from 1 to 15 carbon atoms or perfluorocycloalkyl group having from 1 to 15 carbon atoms.

DETAILED DESCRIPTION OF THE INVENTION

The suitable hexafluoropropene trimers include perfluoro-(4-methyl-3-isopropyl-2-pentene) [hereinafter referred to as "trimer A"], perfluoro-(2,4-dimethyl-3-ethyl-2-pentene) [hereinafter referred to as "trimer B"], and perfluoro-(2,4-dimethyl-3-heptene) [hereinafter referred to as "trimer C"]. Among them, the trimer A and the trimer B are preferred because of their high yield. Other hexafluoropropene trimers will be apparent to one of ordinary skill in the art.

Further, in the present invention, one or more kinds of hexafluoropropene trimers may be used. For example, the trimer may be only the trimer A, only the trimer B, or a mixture of the trimer A and trimer B. The trimer may also be a mixture of the trimer C and trimer A and/B. In this case, the amount of the trimer C is preferably minimized to maintain adequate yields of desired hybrid compounds in the reaction solution.

R in the above general formula (3) may be any alkyl or aryl group having from 1 to 15 carbon atoms. When R is an alkyl group, it may be a straight chain type or a branched type. When R is an aryl group, its aromatic ring may have one or more substituents such as a lower alkyl group having from 1 to 3 carbon atoms, and may be a condensed ring. R is preferably an alkyl group having from 1 to 4 carbon atoms, more preferably, a methyl group, to assure reliable stability of the radical to be produced.

While G in the above general formula (3) may include Li, Na, K, MgX, ZnX, and CdX (wherein X represents Cl, Br and I), and any other metal that its metal complex has ability of releasing carbanions, Li or MgBr is prefered in view of the stability and/or handleability of an associated reagent. Further, in view of the selectivity of the reagent, MgBr is preferred to obtain a monosubstituted compound represented by the general formula (1) or (2) in which one of X, Y and Z is substituted with R, or Li is more preferable to obtain a multisubstituted compound represented by the general formula (1) or (2) in which two or more of X, Y and Z are substituted with R.

While an aprotic polar solvent is preferable as a reaction solvent for use in the perfluoroolefin-hydrocarbon-hybrid-compound producing method of the present invention, the reaction can be conducted without solvent. Suitable aprotic polar solvents include ethers such as diethyl ether, dibutyl ether, tetrahydrofuran or 1,4-dioxane. In particular, diethyl ether (hereinafter referred to as "ether" for brevity) is preferable in view of the yield of a resulting product and/or its high availability even under low temperature conditions. Other suitable aprotic polar solvents and solvents more generally will be apparent to one of ordinary skill in the art.

If a reaction solvent is used, it must be subjected to a strict dehydration treatment under inert gas atmosphere in advance, because the organometallic compound in the perfluoroolefin-hydrocarbon-hybrid-compound producing method of the present invention is reactive to water or oxygen. In addition, during the reaction between the hexafluoropropene trimer and the organometallic compound, the reaction system is preferably controlled under inert gas atmosphere. It should be noted that if the reaction system is exposed to water or oxygen, a desired yield may not be obtained, and an unintended compound may be undesirably produced.

In the perfluoroolefin-hydrocarbon-hybrid-compound producing method of the present invention, the molar ratio of the organometallic compound to the hexafluoropropene trimer is preferably in the range of about 0.2:1 to 10:1, and more preferably about 0.6:1 to 5:1.

The reaction temperature in the perfluoroolefin-hydrocarbon-hybrid-compound producing method of the present invention is typically suitably controlled in the range of a lower limit of about −100° C. to an upper limit of about 40° C. The preferable range of reaction temperature varies according to the kind of the group R in the organometallic compound. For example, when R is a methyl group, the reaction temperature is preferably, but not limited to, the range of about −10 to 10° C., and when R is a butyl or phenyl group, the reaction temperature is preferably, but not limited to, the range of about −70 to −30° C.

While a reaction time in the perfluoroolefin-hydrocarbon-hybrid-compound producing method of the present invention varies according to a molar ratio of the organometallic compound to the hexafluoropropene trimer and other factors, the reaction is substantially completed within several minutes to several dozen hours in any case. In view of a desirable yield and the suppression of by-products, the reaction time is preferably set in the range of about 30 minutes to 24 hours, more preferably about 3 hours to 6 hours.

In the perfluoroolefin-hydrocarbon-hybrid-compound producing method of the present invention, the molar ratio of the organometallic compound to the hexafluoropropene trimer can be selectively determined to produce the perfluoroolefin-hydrocarbon hybrid compound in any form of a monosubstituted compound having one hydrocarbon group or multisubstituted compounds having two or three hydrocarbon group. When only a monosubstituted compound is produced, a molar ratio of the organometallic compound to the hexafluoropropene trimer is preferably in the range of about 0.8:1 to 1.25:1. When a multisubstituted compound is produced, a molar ratio of an organometallic compound to the hexafluoropropene trimer is preferably in the range of about 1.5 or more: 1.

For example, when the trimer A is used as the hexafluoropropene trimer, and methyl lithium is used as the organometallic compound and added to the trimer A in a molar ratio of about 1.21:1.00, the perfluoroolefin-hydrocarbon hybrid compound will be obtained in the form of a mixture consisting of a hybrid compound represented by the general formula (1) (where X, and Y=F; and Z=$CH_3$) and a hybrid compound represented by the general formula (2) (where X, and Y=F; and Z=$CH_3$), with a yield of about 40 to 80%. These hybrid compounds represented by the general formulas (1) and (2) are different only in a double-bond position, and can be interconverted by using a fluorine source such as potassium fluoride. Such hybrid compounds in the form of a mixture can be used to produce the highly stable perfluoroalkyl radical without particular problems.

As another example, when the trimer B is used as the hexafluoropropene trimer, and methyl lithium is used as the organometallic compound and added to the trimer B in a molar ratio of about 1.21:1.00, the perfluoroolefin-hydrocarbon hybrid compound will be obtained in the form of a mixture consisting of a hybrid compound represented by the general formula (1) (where X=$CH_3$; and Y, and Z=F) and a hybrid compound represented by the general formula (2) (where X=$CH_3$; and Y, and Z=F), with a yield of about 40 to 80%. As with the aforementioned example, the hybrid compounds represented by the general formulas (1) and (2) are different only in a double-bond position. While the hybrid compound represented by the above general formula (1) has geometrical isomers (E) and (Z), it can be used to produce the highly stable perfluoroalkyl radical without particular problems.

The highly-stable-perfluoroalkyl-radical producing method of the present invention is characterized by fluorinating the above perfluoroolefin-hydrocarbon hybrid compound to form a highly stable perfluoroalkyl radical represented by the general formula (1R) or (2R).

Any perfluoroolefin-hydrocarbon hybrid compounds represented by the general formulas (1) and (2) can be used in the highly-stable-perfluoroalkyl-radical producing method of the present invention. These compounds can be obtained through the aforementioned perfluoroolefin-hydrocarbon-hybrid-compound producing method of the present invention.

The perfluoroolefin-hydrocarbon hybrid compound to be used is preferably a monosubstituted hybrid compound represented by the general formula (1) or (2) in which one of X, Y and Z is substituted with R, more preferably a hybrid compound represented by the general formula (1) (where X, and Y=F; and Z=R) or the general formula (2) (where X, and Y=F; and Z=R). While a multisubstituted compound represented by the general formula (1) or (2) in which two or more of X, Y and Z are substituted by R or another monosubstituted compound other than the above monosubstituted compound can be fluorinated to form the highly stable perfluoroalkyl radicals, production conditions such as reaction temperature and reaction time to be considered will be inevitably increased to obtain a desired yield.

A mixture consisting of a hybrid compound represented by the general formula (1) (where X, and Y=F; and Z=R) and a hybrid compound represented by the general formula (2) (where X, and Y=F; and Z=R) which are different only in a double-bond position may also be used as the perfluoroolefin-hydrocarbon hybrid compound without particular problems. While the perfluoroolefin-hydrocarbon hybrid compound may also be comprised of two or more kinds of the hybrid compounds each having a different structure, it is desired to use one kind of the hybrid compound to form the highly stable perfluoroalkyl radical with enhanced purity.

The fluorination in the highly-stable-perfluoroalkyl-radical producing method of the present invention is preferably carried out by using fluorine gas. This fluorine gas may or may not be diluted. When the fluorine gas is diluted, an inert gas such as nitrogen or argon may be used. The purity of the fluorine gas is preferably as high as possible.

The fluorination in the highly-stable-perfluoroalkyl-radical producing method of the present invention is typically carried out by bubbling a diluted fluorine gas or non-diluted pure fluorine gas from the bottom of a reaction vessel.

The fluorination provides a highly stable perfluoroalkyl radical having a fluorine atom added to one of the double-bonded carbon atoms in the perfluoroolefin-hydrocarbon hybrid compound, and an unpaired electron on the other double-bonded carbon atom. The above fluorination is occasionally referred to as "direct fluorination" herein.

In the direct fluorination, the bubbling time-period varies according to the kind of the perfluoroolefin-hydrocarbon hybrid compound, the reaction temperature of the fluorination and other factors. In view of the yield of the highly stable perfluoroalkyl radical to be produced, the lower limit of the bubbling period is preferably about 30 minutes, more preferably about 1 hour, particularly about 4 hours, and the upper limit of the bubbling period is preferably about 720 hours, more preferably about 500 hours, particularly about 20 hours. The lower limit of the reaction temperature of the fluorination is preferably about −70° C., more preferably about −30° C., and the upper lower limit of the reaction temperature is preferably about 70° C., more preferably about 40° C. While the fluorination is typically carried out under a pressure of about 1 atm, it may be carried out under a high pressure of greater than about 1 atm. In some cases, a higher pressure may be advantageously selected in view of a reaction rate of the fluorination.

The highly stable perfluoroalkyl radical to be obtained through the highly-stable-perfluoroalkyl-radical producing method of the present invention includes any perfluoroalkyl radical represented by the above general formulas (1R) and (2R).

Rf in the above general formulas (1R) and (2R) includes any perfluoroalkyl or perfluorocycloalkyl group having from 1 to 15 carbon atoms. When Rf is a perfluoroalkyl group, it may be a straight chain type or a branched type. When Rf is a perfluorocycloalkyl group, its cycloalkyl ring may have one or more substituents such as a lower perfluoroalkyl group having from 1 to 3 carbon atoms, and its cycloalkyl ring may be a condensed ring. In view of the stability of the highly stable perfluoroalkyl radical, the substituent is preferably a perfluoroalkyl group having from 1 to 4 carbon atoms, more preferably a trifluoromethyl group.

Ra in the above general formula (1R) and (2R) is a carbon atom having one unpaired electron. The term "carbon atom having one unpaired electron" herein means carbon having an unpaired electron of a free radical on the atom thereof.

Typically, in the highly-stable-perfluoroalkyl-radical producing method of the present invention, under appropriately selected reaction conditions, the perfluoroolefin-hydrocarbon hybrid compound represented by the general formula (1) (where X, and Y=F; and Z=CH$_3$) or the general formula (2) (where X, and Y=F; and Z=CH$_3$) is used to form a highly stable perfluoroalkyl radical represented by the general formula (1R) (where Rf$^1$, and Rf$^2$=F; and Rf$^3$=CF$_3$) as a primary product, or the perfluoroolefin-hydrocarbon hybrid compound represented by the general formula (1) (where X=CH$_3$; and Y, and Z=F) or the general formula (2) (where X=CH$_3$; and Y, and Z=F) is used to form a highly stable perfluoroalkyl radical represented by the general formula (1R) (where Rf$^1$CF$_3$; and Rf$^2$, and Rf$^3$=F) as a primary product.

As described above, the perfluoroolefin-hydrocarbon hybrid compound according to the present invention is a novel compound having the above chemical structure, and can be used as a precursor for the highly stable perfluoroalkyl radicals.

The highly-branched-perfluoroolefin-hydrocarbon-hybrid-compound producing method of the present invention allows the highly branched perfluoroolefin-hydrocarbon hybrid compound to be produced through a simplified process with enhanced yield by using low-cost compounds as starting materials.

The highly-stable-perfluoroalkyl-radical producing method of the present invention allows the highly stable perfluoroalkyl radical to be produced through a simplified process with enhanced yield and purity. In addition, this method is suitable for industrial use requiring a large-scale synthesis because of easiness in scale-up on the reaction therein.

The highly stable perfluoroalkyl radical to be obtained by the method of the present invention has the unique characteristics of (1) excellent chemical stability or inertness to active chemical species such as acid, alkali or water, (2) isolatability through dispersion gas chromatography or the like, and (3) releasability of low molecular weight perfluoroalkyl radicals such as trifluoromethyl at a temperature of about 90° C. or more. For example, the perfluoroalkyl radical obtained through the method of the present invention can be advantageously used as a polymerization initiator in an organic synthesis reaction.

Specifically, the perfluoroalkyl radical controlled at a given temperature is added into a reaction system, and then adjusted at a temperature of about 90° C. or more to allow low molecular weight radicals to be released therefrom.

EXAMPLES

While the present invention will now be described in more detail in conjunction with various Examples, it should be understood that the present invention is not construed as being limited to these Examples. Unless otherwise indicated, all the parts and percents are by weight. A $^{19}$F-NMR (282.24 MHz) described in the Examples was measured by using deuterated chloroform as a solvent and fluoroform (CFCl$_3$) as an internal reference. A chemical shift value in the $^{19}$F-NMR was expressed by δppm on the presumption that an absorption magnetic field higher than that of fluoroform is defined as minus.

A $^1$H-NMR (299.95 MHz) was measured by using deuterated chloroform as a solvent and tetramethylsilane as an internal reference. A chemical shift value in the $^1$H-NMR was represented by δppm on the presumption that an absorption magnetic field higher than that of tetramethylsilane is defined as minus. A gas chromatography measurement was carrier out by using a capillary column (NB-1, 0.25 μm, 1.5 mm Φ×60 m) and a TCD as a detector. A mass spectrum (MS) was measured by using a gas chromatography-quadrupole mass spectrometer (GC-MS) at an ionization potential of 70 eV.

Example 1

Synthesis of 2-methyl-perfluoro-(4-methyl-3-isopropyl-2-pentene) and 4-methyl-perfluoro-(2-methyl-3-isopropyl-2-pentene) [Reaction with Lithium Reagent]

Under argon atmosphere, 1.9 mmol (852 mg) of hexafluoropropene trimer mixture [including 5 wt % of perfluoro-(3-ethyl-2,4-dimethyl-2-pentene)] comprising perfluoro-(4-methyl-3-isopropyl-2-pentene) as a main component was put in a 100 ml egg-plant-shaped flask with a three-way stopcock having a magnet stirrer made of Teflon (R) therein. Then, 10 ml of anhydrous ether dry-distilled on sodium was added into the mixture, and stirringly dissolved therein. 1.5 ml (2.3 mmol) of ether solution containing 1.5M methyl lithium—lithium bromide complex was dropped into the mixture from a dropping funnel in the interval of about 5 minutes, while maintaining the mixture at about 0° C. by cooling the reaction vessel in ice. When the reaction is completed after continuously stirring at about 0° C. for about 5 hours, the resulting reacted mixture became a white suspension. Then, the reaction vessel was returned to room temperature, and the solvent and products were subjected to distillation under a vacuum of 1 mmHg to remove a solid component. The distilled component was subjected to re-distillation under normal pressure to remove the ether solvent. As a result, a mixture of 2-methyl-perfluoro-(4-methyl-3-isopropyl-2-pentene) and 4-methyl-perfluoro-(2-methyl-3-isopropyl-2-pentene) was obtained. The respective structures of the obtained compounds were determined by the $^{19}$F—NMR, $^1$H—NMR, GC—MS and others. The yields of 2-methyl-perfluoro-(4-methyl-3-isopropyl-2-pentene) and 4-methyl-perfluoro-(2-methyl-3-isopropyl-2-pentene) calculated from the integral ratio of the peak areas of the NMR spectrums were about 45% and 19%, respectively.

The 2-methyl-perfluoro-(4-methyl-3-isopropyl-2-pentene) had the following physical properties.

$^{19}$F—NMR: −58.33 (3F, Doublet, J=63.5 Hz), −69.71 (6F, singlet), −71.92 (6F, doublet, J=37.8 Hz), −163.72 (1F, quartet doublet, J=64.9, 10.4 Hz), −164.34 (1F, septet doublet, J=38.1 10.4 Hz)

$^1$H—NMR: 2.21 (singlet)

MS (m/z, %): 407 (M—H−2F, 2.9), 377 (M-CF$_3$, 3.3), 357 (C$_9$H$_2$F$_{13}$, 1.9), 319 (C$_9$H$_2$F$_{11}$, 4.9), 293 (C$_7$F$_{11}$, 4.2), 181 (C$_4$F$_7$, 5.1), 69 (F$_3$, 100), 65 (C$_2$H$_3$F$_2$, 34), 51 (CHF$_2$, 27)

The 4-methyl-perfluoro-(2-methyl-3-isopropyl-2-pentene) had the following physical properties.

$^{19}$F—NMR: -56.53 (3F, broad doublet, J=63.5 Hz), −57.18 (3F, multiplet), −69.09 (3F, broad doublet, J=27.7 Hz), −70.36 (3F, broad doublet, J=33.0 Hz), −138.45 (1F, multiplet), 156.31 (1F, quartet doublet, J=53.3, 12.1 Hz)

$^1$H—NMR: 2.02 (doublet, J=25.5 Hz)

MS (m/z, %): 407 (M—H−2F, 2.5), 319 (C$_9$H$_2$F$_{11}$, 4.3), 277 (C$_7$H$_3$F$_{10}$, 1.9), 257 (C$_7$H$_2$F$_9$, 4.0), 225 (C$_6$HF$_8$, 8.7), 119 (C$_2$F$_5$, 5.5), 69 (CF$_3$, 100), 51 (CHF$_2$,30)

Example 2

Synthesis of 2-methyl-perfluoro-(4-methyl-3-isopropyl-2-pentene) and 4-methyl-perfluoro-(2-methyl-3-isopropyl-2-pentene) [Reaction with Grignard Reagent]

Under argon atmosphere, 1.5 mmol (675 mg) of hexafluoropropene trimer mixture [including 5 wt % of perfluoro-(3-ethyl-2,4-dimethyl-2-pentene)] comprising perfluoro-(4-methyl-3-isopropyl-2-pentene) as a main component was put in a 100 ml egg-plant-shaped flask with a three-way stopcock having a magnet stirrer made of Teflon (R) therein. Then, 10 ml of anhydrous ether dry-distilled on sodium was added into the mixture, and stirringly dissolved therein. 0.6 ml (1.8 mmol) of ether solution containing a 1.5M Grignard reagent was dropped into the mixture from a dropping funnel in the interval of about 2 minutes, while maintaining the mixture at about 0° C. by cooling the reaction vessel in ice. When the reaction is completed after continuously stirring at about 0° C. for about 5 hours, the resulting reacted mixture became a white suspension. Then, the reaction vessel was returned to room temperature, and the solvent and products were subjected to distillation under a vacuum of 1 mmHg to remove a solid component. The distilled component was subjected to re-distillation under normal pressure to remove the ether solvent. As a result, a mixture of 2-methyl-perfluoro-(4-methyl-3-isopropyl-2-pentene) and 4-methyl-perfluoro-(2-methyl-3-isopropyl-2-pentene) was obtained. The respective structures of the obtained compounds were determined by the $^{19}$F—NMR, $^1$H—NMR, GC—MS and others. The yields of 2-methyl-perfluoro-(4-methyl-3-isopropyl-2-pentene) and 4-methyl-perfluoro-(2-methyl-3-isopropyl-2-pentene) calculated from the integral ratio of the peak areas of the NMR spectrums were about 13% and 45%, respectively.

Example 3

Synthesis of 4-methyl-perfluoro-(4-methyl-3-isopropyl-2-pentene) and 4-methyl-perfluoro-(3-ethyl-2,4-dimethyl-2-pentene)

Under argon atmosphere, 1.00 mmol (453 mg) of perfluoro-(3-ethyl-2,4-dimethyl-2-pentene) was put in a 100 ml egg-plant-shaped flask with a three-way stopcock having a magnet stirrer made of Teflon (R) therein. Then, 10 ml of anhydrous ether dry-distilled on sodium was added into the mixture, and stirringly dissolved therein. 1.5 ml (2.3 mmol) of ether solution containing 1.5M methyl lithium—lithium bromide complex was dropped into the mixture from a dropping funnel in the interval of about 5 minutes, while maintaining the mixture at about 0° C. by cooling the reaction vessel in ice. When the reaction was completed after continuously stirring at about 0° C. for about 5 hours, the resulting reacted mixture became a white suspension. Then, the reaction vessel was returned to room temperature, and the solvent and products were subjected to distillation under a vacuum of 1 mmHg to remove a solid component. The distilled component was subjected to re-distillation under normal pressure to remove the ether solvent. As a result, a mixture of 4-methyl-perfluoro-(4-methyl-3-isopropyl-2-pentene) and 4-methyl-perfluoro-(3-ethyl-2,4-dimethyl-2-pentene) was obtained. The respective structures of the obtained compounds were determined by the $^{19}$F-NMR, $^1$H-NMR, GC-MS and others. The yields of (E)-4-methyl-perfluoro-(4-methyl-3-isopropyl-2-pentene), (Z)-4-methyl-perfluoro-(4-methyl-3-isopropyl-2-pentene) and 4-methyl-perfluoro-(3-ethyl-2,4-dimethyl-2-pentene) calculated from the integral ratio of the peak areas of the NMR spectrums were about 22%, 26% and 10%, respectively. About 11% of perfluoro-(3-ethyl-2,4-dimethyl-2-pentene) of the raw material was also collected.

The (E)-4-methyl-perfluoro-(4-methyl-3-isopropyl-2-pentene) has the following physical properties.

$^{19}$F—NMR: −62.70 (3F, doublet, J=58.4 Hz), −67.90 (6F, doublet, J=41.8 Hz), −70.52 (6F, singlet), −72.29 (1F, septet doublet, J=41.5, 9.6 Hz), −160.66 (1F, septet doublet, J=58.5, 10.4 Hz)

$^1$H—NMR: 1.80 (singlet)

MS (m/z, %): 357 ($C_9H_2F_{13}$, 1.9), 289 ($C_8H_3F_{10}$, 2.4), 269 ($C_8H_2F_9$, 5.2), 263 ($C_6HF_{10}$, 7.6), 243 ($C_6F_9$, 3.1), 195 ($C_5H_2F_7$, 2.4), 181 ($C_4F_7$, 2.9), 164 ($C_4H_2F_6$, 7.4), 119 ($C_2F_5$, 6.5), 95 ($C_3H_2F_3$, 5.9), 77 ($C_3H_3F_2$, 5.1), 69 ($CF_3$, 100), 65 ($C_2H_3F_2$, 31), 51 ($CHF_2$, 15)

The (Z)-4-methyl-perfluoro-(4-methyl-3-isopropyl-2-pentene) had the following physical properties.

$^{19}$F-NMR: −59.21 (3F, singlet), −66.11 (6F, doublet, J=38.1 Hz), −71.98 (6F, doublet, J=35.8 Hz), −74.35 (1F, septet doublet, J=37.8, 15.2 Hz), −166.75 (1F, septet doublet, J=38.1, 15.2 Hz)

$^1$H-NMR: 1.96 (singlet)

MS (m/z, %): 357 ($C_9H_2F_{13}$, 1.9), 289 ($C_8H_3F_{10}$, 2.5), 269 ($C_8H_2F_9$, 4.9), 263 ($C_6HF_{10}$, 4.1), 243 ($C_6F_9$, 2.2), 219 ($C_4F_9$, 2.1), 195 ($C_5H_2F_7$, 2.0), 181 ($C_4F_7$, 2.5), 164 ($C_4H_2F_6$, 7.7), 119 ($C_2F_5$, 6.0), 95 ($C_3H_2F_3$, 6.0), 77 ($C_3H_3F_2$, 6.0), 69 ($CF_3$, 100), 65 ($C_2H_3F_2$, 32), 51 ($CHF_2$, 14)

The 4-methyl-perfluoro-(3-ethyl-2,4-dimethyl-2-pentene) has the following physical properties.

$^{19}$F-NMR: −53.2 (3F, broad singlet), −58.7 (3F, broad singlet), −57 ~−59 (6F, broad multiplet), −66 ~−68 (3F, broad multiplet), −89 ~−91 (2F, broad multiplet)

$^1$H-NMR: 2.00 (singlet)

MS (m/z, %): 357 ($C_9H_2F_{13}$, 1.1), 289 ($C_8H_3F_{10}$, 2.7), 269 ($C_8H_2F_9$, 3.8), 263 ($C_6HF_{10}$, 8.9), 243 ($C_6F_9$, 2.5), 219 ($C_4F_9$, 2.0), 181 ($C_4F_7$, 3.3), 164 ($C_4H_2F_6$, 6.2), 119 ($C_2F_5$, 5.3), 77 ($C_3H_3F_2$, 3.9), 69 ($CF_3$, 100), 65 ($C_2H_3F_2$, 23), 51 ($CHF_2$, 8.5)

Example 4

Synthesis of 2,4-dimethyl-perfluoro-(4-methyl-3-isopropyl-2-pentene), 3-[1,1-bis(trifluoromethyl) ethyl]-4-methyl-perfluoro-(4-methyl-2-pentene) and 3-[1,1-bis(trifluoromethyl) ethyl]-2,4-dimethyl-perfluoro-(4-methyl-2-pentene)

Under argon atmosphere, 1.00 mmol (453 mg) of perfluoro-(3-ethyl-2,4-dimethyl-2-pentene) was put in a 100 ml egg-plant-shaped flask with a three-way stopcock having a magnet stirrer made of Teflon (R) therein. Then, 10 ml of anhydrous ether dry-distilled on sodium was added into the mixture, and stirringly dissolved therein. 2.4 ml (3.6 mmol) of ether solution containing 1.5M methyl lithium—lithium bromide complex was dropped into the mixture from a dropping funnel in the interval of about 10 minutes, while maintaining the mixture at about 0° C. by cooling the reaction vessel in ice. When the reaction is completed after continuously stirring at about 0° C. for about 5 hours, the resulting reacted mixture became a white suspension. Then, the reaction vessel was heated up to about 50° C., and the solvent and products were subjected to distillation under a vacuum of 1 mmHg to remove a solid component. The distilled component was subjected to re-distillation under normal pressure to remove the ether solvent. As a result, a mixture of 2,4-dimethyl-perfluoro-(4-methyl-3-isopropyl-2-pentene), 3-[1,1-bis(trifluoromethyl) ethyl]-4-methyl-perfluoro-(4-methyl-2-pentene) and 3-[1,1-bis (trifluoromethyl) ethyl]-2,4-dimethyl-perfluoro-(4-methyl-2-pentene) was obtained. The respective structures of the obtained compounds were determined by the $^{19}$F-NMR, $^1$H-NMR, GC-MS and others. The yields of (Z)-2,4-dimethyl-perfluoro-(4-methyl-3-isopropyl-2-pentene), (E)-2,4-dimethyl-perfluoro-(4-methyl-3-isopropyl-2-pentene), 3-[1,1-bis(trifluoromethyl)ethyl]-4-methyl-perfluoro-(4-methyl-2-pentene) and 3-[1,1-bis(trifluoromethyl)ethyl]-2,4-dimethyl-perfluoro-(4-methyl-2-pentene) calculated from the integral ratio of the peak areas of the NMR spectrums were about 13%, 16%, 17% and 28%, respectively. About 27% of (E)-4-methyl-perfluoro-(4-methyl-3-isopropyl-2-pentene) was also created.

The (Z)-2,4-dimethyl-perfluoro-(4-methyl-3-isopropyl-2-pentene) had the following physical properties.

$^{19}$F-NMR: −61.94 (3F, doublet, J=53.3 Hz), −64.18 (6F, singlet), −68.39 (6F, singlet), −146.05 (1F, quartet, J=55.0 Hz)

$^1$H-NMR: 1.84 (3H, multiplet), 2.29 (3H, multiplet)

MS (m/z, %): 383 ($C_{11}H_4F_{13}$, 2.1), 363 ($C_{11}H_3F_2$, 1.6), 353 ($C_{10}H_5F_{12}$, 6.8), 333 ($C_{10}H_4F_{11}$, 7.5), 313 ($C_{10}H_3F_{10}$, 7.6), 283 ($C_9H_4F_9$, 5.1), 263 ($C_9H_3F_8$, 7.3), 245 ($C_9H_4F_7$, 5.8), 225 ($C_9H_3F_6$, 11), 213 ($C_8H_3F_6$, 6.7), 195 ($C_5H_2F_7$, 5.7), 189 ($C_3HF_8$, 7.3), 163 ($C_4BF_6$, 7.1), 146 ($C_4H_3F_5$, 10), 145 ($C_4H_2F_5$, 19), 127 ($C_4H_3F_4$, 5.6), 119 ($C_2F_5$, 6.9), 113 ($C_3HF_4$, 6.5), 95 ($C_3H_2F_3$, 10), 77 ($C_3H_3F_2$, 17), 69 ($CF_3$, 100), 65 ($C_2H_3F_2$, 58), 51 ($CHF_2$, 38)

The (E)-2,4-dimethyl-perfluoro-(4-methyl-3-isopropyl-2-pentene) had the following physical properties.

$^{19}$F-NMR: −64.04 (6F, multiplet), −64.75 (3F, septet, J=15.5 Hz), −70.10 (6F, multiplet), 150.71 (1F, broad singlet)

$^1$H-NMR: 1.91 (3H, singlet), 2.33 (3H, singlet)

MS (m/z, %): 383 ($C_{11}H_4F_{13}$, 2.1), 363 ($C_{11}H_3F_{12}$, 1.6), 353 ($C_{10}H_5F_{12}$, 6.8), 333 ($C_{10}H_4F_1$, 7.5), 313 ($C_{10}H_3F_{10}$, 7.6), 283 ($C_3H_4F_9$, 5.1), 263 ($C_9H_3F_8$, 7.3), 245 ($C_9H_4F_7$, 5.8), 225 ($C_9H_3F_6$, 11), 213 ($C_8H_3F_6$, 6.7), 195 ($C_5H_2F_7$, 5.7), 189 ($C_3HF_8$, 7.3), 163 ($C_4HF_6$, 7.1), 146 ($C_4H_3F_5$, 10), 145 ($C_4H_2F_5$, 19), 127 ($C_4H_3F_4$, 5.6), 119 ($C_2F_5$, 6.9), 113 ($C_3HF_4$, 6.5), 95 ($C_3H_2F_3$, 10), 77 ($C_3H_3F_2$, 17), 69 ($CF_3$, 100), 65 ($C_2H_3F_2$, 58), 51 ($CHF_2$, 38)

The 3-[1,1-bis (trifluoromethyl) ethyl]-4-methyl-perfluoro-(4-methyl-2-pentene) had the following physical properties.

$^{19}$F-NMR: −59.66 (3F, broad), −63.11 (6F, singlet), −66.40 (6F, doublet, J=46.3 Hz), −72.04 (1F, multiplet)

$^1$H-NMR: 1.92 (3H, multiplet), 1.99 (3H, singlet)

MS (m/z, %): 353 ($C_{10}H_5F_{12}$, 2.2), 277 ($C_{10}H_5F_8$, 2.3), 263 ($C_9H_3F_8$, 3.2), 239 ($C_{10}H_5F_6$, 2.3), 213 ($C_8H_3F_6$, 3.6), 207 ($C_9H_4F_5$, 2.3), 195 ($C_5H_2F_7$, 3.7), 163 ($C_4HF_6$, 3.1), 145 ($C_4H_2F_5$, 11), 119 ($C_2F_5$, 4.7), 113 ($C_3BF_4$, 3.2), 95 ($C_3H_2F_3$, 6.3), 77 ($C_3H_3F_2$, 11), 69 ($CF_3$, 100), 51 ($CHF_2$, 18)

The 3-[1,1-bis (trifluoromethyl) ethyl]-2,4-dimethyl-perfluoro-(4-methyl-2- pentene) had the following physical properties.

$^{19}$F-NMR: −64.95 (3F, multiplet), −68.68 (6F, singlet), −70.85 (6F, singlet)

$^1$H-NMR: 1.58 (3H, singlet), 1.71 (3H, singlet), 2.93 (3H, singlet) MS (m/z, %): 422 ($C_{11}H_5F_{15}$, 5.8), 403 ($C_{11}H_5F_{14}$, 5.1), 383 ($C_{11}H_4F_{13}$, 5.1), 363 ($C_{11}H_3F_{12}$, 2.4), 353 ($C_{10}H_5F_{12}$, 13), 333 ($C_{10}H_4F_1$, 31), 313 ($C_{10}H_3F_{10}$, 16), 293 ($C_{10}H_2F_9$, 6.8), 263 ($C_9H_3F_8$, 10), 257 ($C_7H_2F_9$, 5.9), 195 ($C_5H_2F_7$, 5.7), 170 ($C_3HF_7$, 5.7), 169 ($C_3F_7$, 6.2), 145 ($C_4H_2F_5$, 62), 119 ($C_2F_5$, 8.7), 113 ($C_3HF_4$, 5.8), 101 ($C_2BF_4$, 5.9), 95 ($C_3H_2F_3$, 14), 77 ($C_3H_3F_2$, 5.8), 75 ($C_3HF_2$, 9.8), 69 ($CF_3$, 100), 65 ($C_2H_3F_2$, 58), 50 ($CF_2$, 26)

Example 5

Synthesis of 2-butyl-perfluoro-(4-methyl-3-isopropyl-2-pentene) and 4-butyl-perfluoro-(2-methyl-3-isopropyl-2-pentene)

Under argon atmosphere, 1.0 mmol (452 mg) of hexafluoropropene trimer mixture [including 5 wt % of perfluoro-(3-ethyl-2,4-dimethyl-2-pentene)] comprising perfluoro-(4-methyl-3-isopropyl-2-pentene) as a main component was put in a 100 ml egg-plant-shaped flask with a three-way stopcock having a magnet stirrer made of Teflon (R) therein. Then, 10 ml of anhydrous ether dry-distilled on sodium was added into the mixture, and stirringly dissolved therein. 1.0 ml (1.1 mmol) of hexane solution containing 10% of butyl lithium was dropped into the mixture from a dropping funnel in the interval of about 3 minutes, while maintaining the mixture at about −78° C. by cooling the reaction vessel in a dry ice-ethanol bath. After continuously stirring at about −50° C. for about 3 hours, the resulting reacted mixture became a yellow solution. Then, a small amount of distilled water was added to the reaction mixture to decompose unreacted butyl lithium, and the reacted mixture was dried by magnesium sulfate. After drying for one night, the ether solvent and hexane was removed from the reaction mixture under normal pressure, and the resulting mixture was subjected to distillation under a vacuum of 10 mmHg. As a result, a mixture of 2-butyl-perfluoro-(4-methyl-3-isopropyl-2-pentene) and 4-butyl-perfluoro-(2-methyl-3-isopropyl-2-pentene) was obtained. The respective structures of the obtained compounds were determined by the $^{19}$F-NMR, $^1$H-NMR, GC-MS and others. The yields of 2-butyl-perfluoro-(4-methyl-3-isopropyl-2-pentene) and 4-butyl-perfluoro-(2-methyl-3-isopropyl-2-pentene) calculated from the integral ratio of the peak areas of the capillary gas chromatographies were about 44% and 2.0%, respectively.

The 2-butyl-perfluoro-(4-methyl-3-isopropyl-2-pentene) had the following physical properties.

$^{19}$F-NMR: −55.83 (3F, doublet, J=63.8 Hz), −70.32 (6F, singlet), −71.74 (6F, doublet, J=38.1 Hz), −162.62 (1F, quartet doublet, J=61.8, 11.9 Hz), −163.63 (1F, septet doublet, J=37.8, 11.9 Hz)

$^1$H-NMR: 0.96 (3H, multiplet), 1.2~1.6 (8H, multiplet), 1.55 (2H, multiplet)

MS (m/z, %): 449 (M-H-$_2F_3$, 1.9), 429 ($Cl_3H_7F_{14}$, 3.3), 269 ($C_5F_1$, 2.1), 181 ($C_4F_7$, 2.4), 169 ($C_3F_7$, 2.1), 163 ($C_4HF_6$, 3.0), 145 ($C_4H_2F_5$, 2.8), 119 ($C_2F_5$, 3.3), 113 ($C_3HF_4$, 2.4), 69 ($CF_3$, 73), 65 ($C_2H_3F_2$, 23), 56 ($C_4H_8$, 100), 55 ($C_4H_7$, 15), 51 ($CHF_2$, 17)

The 4-butyl-perfluoro-(2-methyl-3-isopropyl-2-pentene) had the following MS spectrum data.

MS (m/z, %): 399 ($C_{12}H_8F_{13}$, 3.2), 381 ($C_2H_9F_{12}$, 3.4), 205 ($C_4H_5F_8$, 5.1), 181 ($C_4F_7$, 6.7), 169 ($C_3F_7$, 4.3), 163 ($C_4HF_6$, 4.8), 145 ($C_4H_2F_5$, 6.68), 73 ($C_4H_6F$, 8.5), 69 ($CF_3$, 45), 65 ($C_2H_3F_2$, 13), 61 ($C_3HF$, 14), 56 ($C_4H_8$, 100), 55 ($C_4H_7$, 22), 51 ($CHF_2$, 9.0)

Example 6

Synthesis of 2-phenyl-perfluoro-(4-methyl-3-isopropyl-2-pentene) and Isomers Thereof Under argon atmosphere, 1.0 mmol (459 mg) of hexafluoropropene trimer mixture [including 5 wt % of perfluoro-(3-ethyl-2,4-dimethyl-2-pentene)] comprising perfluoro-(4-methyl-3-isopropyl-2-pentene) as a main component was put in a 100 ml egg-plant-shaped flask with a three-way stopcock having a magnet stirrer made of Teflon (R) therein. Then, 10 ml of anhydrous ether dry-distilled on sodium was added into the mixture, and stirringly dissolved therein. 0.5 ml (1.0 mmol) of cyclohexane-ether solution containing 17% of phenyl lithium was dropped into the mixture from a dropping funnel in the interval of about 3 minutes, while maintaining the mixture at about −78° C. by cooling the reaction vessel in a dry ice-ethanol bath. After continuously stirring at about −50° C. for about 3 hours, the resulting reacted mixture became a yellow solution including a brown solid. The reaction mixture was poured into 30 ml of ice water. Then, 20 ml of ether was added therein to extract a target compound, and the extracted compound was rinsed with 30 ml of salt solution. After the reacted ether mixture was dried with magnesium sulfate for one night, the resulting mixture was subjected to reduced-pressure distillation under a vacuum of 5 mmHg to remove ether, and then subjected to reduced-pressure distillation under a vacuum of 10 mmHg. As a result, a mixture of 3 different conformational isomers of 2-phenyl-perfluoro-(4-methyl-3-isopropyl-2-pentene) was obtained. The respective structures of the obtained compounds were determined by $^{19}$F-NMR, $^1$H-NMR, GC-MS and others. The yields of conformational isomers A, B and C of 2-phenyl-perfluoro-(4-methyl-3-isopropyl-2-pentene) calculated from the integral ratio of the peak areas of the $^{19}$F-NMR spectrum were about 24%, 16% and 12%, respectively.

The 2-phenyl-perfluoro-(4-methyl-3-isopropyl-2-pentene) had the following $^1$H-NMR spectrum data and MS spectrum data.

$^1$H-NMR: 7.1~7.7 (multiplet)

MS (m/z, %): 508 ($C_{15}H_5F_{17}$, 92), 469 ($C_{15}H_4F_{15}$, 39), 439 ($C_{14}H_5F_{14}$, 43), 419 ($C_{14}H_4F_{13}$, 100), 399 ($C_{14}H_3F_{12}$, 37), 369 ($C_7F_{15}$, 45), 350 ($C_7F_{14}$, 12), 331 ($C_7F_{13}$, 31), 319 ($C_6F_{13}$, 12), 301 ($C_6HF_{12}$, 26), 300 ($C_6F_{12}$, 48), 281 ($C_6F_{11}$,

50), 270 ($C_5HF_{11}$, 12), 251 ($C_5HF_{10}$, 24), 250 ($C_5F_{10}$, 89), 232 ($C_5HF_9$, 18), 231 ($C_5F_9$, 30), 201 ($C_4HF_8$, 55), 200 ($C_4F_8$, 15), 182 ($C_4HF_7$, 40), 151 ($C_3HF_6$, 45), 69 ($CF_3$, 58), 51 ($CHF_2$, 17)

The conformational isomer A of 2-phenyl-perfluoro-(4-methyl-3-isopropyl-2-pentene) had the following $^{19}$F-NMR spectrum data.

$^{19}$F-NMR: −63.16 (3F, septet, J=16.2 Hz), −69.87 (6F, multiplet), −71.77 (6F, doublet, J=39.8), −151.74 (1F, doublet, J=10.4 Hz), −157.14 (1F, septet doublet, J=39.5, 10.4 Hz)

The conformational isomer B of 2-phenyl-perfluoro-(4-methyl-3-isopropyl-2-pentene) had the following $^{19}$F-NMR spectrum data.

$^{19}$F-NMR: −55.98 (3F, doublet, J=63.8 Hz), −72.06 (6F, singlet), −72.70 (6F, doublet, J=32.7 Hz), −162.01 (1F, quartet, J=65.5 Hz), −169.88 (1F, septet, J=32.7 Hz)

The conformational isomer C of 2-phenyl-perfluoro-(4-methyl-3-isopropyl-2-pentene) had the following $^{19}$F-NMR spectrum data.

$^{19}$F-NMR: −59.21 (3F, doublet, J=56.7 Hz), −69.96 (6F, singlet), −71.36 (6F, doublet, J=37.8 Hz), −165.71 (1F, quartet, J=55.0 Hz), −164.11 (1F, septet, J=39.5Hz)

Example 7

Synthesis of Perfluoro-(2,4-dimethyl-3-isopropyl-3-pentyl) through Direct-Fluorination (at Room Temperature) of 2-methyl-perfluoro-(4-methyl-3-isopropyl-2-pentene) and 4-methylperfluoro-(2-methyl-3-isopropyl-2-pentene)

2.25 g (5.0 mmol) of the mixture of 2-methyl-perfluoro-(4-methyl-3-isopropyl-2-pentene) and 4-methyl-perfluoro-(2-methyl-3-isopropyl-2-pentene) obtained in Example 1 and 10 mL of FC 72 (perfluoroalkane solution containing perfluoro-n-hexane as a primary component) were put in a 20 mL Hauk cylinder. After a magnetic stirrer made of Teflon(R) was inserted into the cylinder, the cylinder was connected to a fluorine line. The cylinder was cooled with liquid nitrogen, and the inner pressure was reduced by a vacuum pump. After three times of a freeze-and-thaw routine, the inner atmosphere was substituted with nitrogen.

Then, pure fluorine gas was introduced from the fluorine line, and the reaction was carried out at room temperature under a pressure of 1 atm while stirring the mixture. The reaction was carried on for 10 days, and then the reacted solution was taken out of the cylinder to determine the respective structures of resulting compounds by GC-MS, ESR and the like. The yield of perfluoro-(2,4-dimethyl-3-isopropyl-3-pentyl) calculated from the peak area ratio of the capillary gas chromatographies was about 75%. Perfluoro-(2,4-dimethyl-3-isopropylpentane) in a saturated form was also created with a yield of about 23%.

Example 8

Synthesis of Perfluoro-(2,4-dimethyl-3-isopropyl-2-pentyl) and Perfluoro-(2,4-dimethyl-3-isopropyl-2-pentene) through Direct-Fluorination (at 0° C.) of 2,4-dimethyl-perfluoro-(4-methyl-3-isopropyl-2-pentene) and 3-[1,1-bis(trifluoro-methyl)ethyl]-4-methyl-perfluoro-(4-methyl-2-pentene)

A mixture (having a purity of about 85% given by dispersion gas chromatography) (44.2 mg, 0.10 mmol) of 2,4-dimethyl-perfluoro-(4-methyl-3-isopropyl-2-pentene) and 3-[1,1-bis(trifluoromethyl) ethyl]-4-methyl-perfluoro-(4-methyl-2-pentene) obtained in Example 4 was put in a 10 mL reacting vessel made of Teflon(R), and dissolved in 5 ml of FC-72. A magnetic stirrer made of Teflon(R) was inserted into the vessel, and a fluorine gas feeding tube was placed on the bottom of the vessel. The reaction vessel was kept at about 0° C. by cooling in ice. Then, pure fluorine gas was introduced in the vessel, and the reaction was carried on for about 72 hours while stirring the mixture. Based on the gas chromatography analysis of the reacted solution, it was proved that about 25% of the raw materials was consumed, and converted into a highly stable perfluoroalkyl radical of perfluoro-(2,4-dimethyl-3-isopropyl-3-pentyl) and perfluoro-(2,4-dimethyl-3-isopropyl-2-pentene). Their yields with respect to the consumed raw materials were about 24% and 43%, respectively.

As mentioned above, according to the perfluoroolefin-hydrocarbon-hybrid-compound producing method of the present invention, a perfluoroolefin-hydrocarbon hybrid compound can be obtained with enhanced yield through a simplified process by using a hexafluoropropene trimer and an organometallic compound of alkali metal or alkali earth metal, which are commercially available at low cost, as starting materials. Further, according to the highly-stable-perfluoroalkyl-radical producing method of the present invention, various kinds of highly stable perfluoroalkyl radicals can be obtained easily with enhanced yield by appropriately selecting the organometallic compound and reaction conditions. A highly stable perfluoroalkyl radical of the present invention has characteristics useful as a reaction initiator in organic synthetic reaction, such as high chemical stability and radical releasability induced by heating.

Although the invention has been described with respect to specific embodiments, the details are not to be construed as limitations, for it will become apparent that various embodiments, changes and modifications may be resorted to without departing from the spirit and scope thereof, and it is understood that such equivalent embodiments are intended to be included within the scope of this invention.

What is claimed is:

1. A perfluoroolefin-hydrocarbon hybrid compound represented by the following general formula (1):

$$[(CF_3)_2CX][(CF_3)_2CY]C=C(CF_3)Z \qquad (1)$$

wherein X, Y and Z may be the same or different, and independently represent F or R, except that all of X, Y and Z are F, wherein R represents straight chain or branched alkyl having from 1 to 15 carbon atoms and aryl groups having from 1 to 15 carbon atoms.

2. A perfluoroolefin-hydrocarbon hybrid compound represented by the following general formula (2):

$$[(CF_3)_2CX][(CF_3)YZ]C=C(CF_3)_2 \qquad (2)$$

wherein X, Y and Z may be the same or different, and independently represent F or R, except that all of X, Y and Z are F, wherein R represents straight chain or branched alkyl having from 1 to 15 carbon atoms and aryl groups having from 1 to 15 carbon atoms.

* * * * *